United States Patent [19]

Cairns et al.

[11] Patent Number: 4,980,354
[45] Date of Patent: Dec. 25, 1990

[54] TETRAHYDRONAPHTHALENE AND INDANE DERIVATIVES

[75] Inventors: James Cairns, Cumbernauld; Duncan R. Rae, Lanark, both of Scotland

[73] Assignee: Akzo N.V., Arnhem, Netherlands

[21] Appl. No.: 408,171

[22] Filed: Sep. 14, 1989

[30] Foreign Application Priority Data

Sep. 19, 1988 [EP] European Pat. Off. ....... 88.308640.7

[51] Int. Cl.$^5$ ................. A61K 31/495; A61K 31/135; C07D 295/00; C07C 211/00
[52] U.S. Cl. .................... 514/255; 544/403; 564/336; 564/378; 514/649; 514/654; 514/657
[58] Field of Search .............. 544/403; 514/255, 649, 514/654, 657; 564/336, 378

[56] References Cited

U.S. PATENT DOCUMENTS

| | | | |
|---|---|---|---|
| 3,621,101 | 11/1971 | Peterson et al. | 514/650 |
| 3,886,168 | 3/1988 | Himmele et al. | 546/205 |
| 4,505,932 | 3/1985 | DeBernardis et al. | 514/649 |

FOREIGN PATENT DOCUMENTS 0259782 5/1975 European Pat. Off.

OTHER PUBLICATIONS

Jerry March, Advanced Organic Chemistry, 3rd Edition, pp. 814–815 and 1099.

Primary Examiner—Cecilia Shen
Attorney, Agent, or Firm—William M. Blackstone; Donna Bobrowicz

[57] ABSTRACT

The invention relates to tetrahydronaphthalene and indane derivatives with the general formula I:

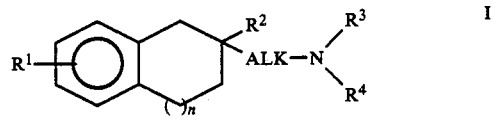

wherein
$R^1$ represents zero to four substituents, which may be the same or different and are selected from OH, halogen, $NO_2$, CN, $CF_3$, $C_1$–$C_4$ alkyl, $C_1$–$C_4$ alkoxy and unsubstituted or $C_1$–$C_4$ alkyl substituted amino;
$R^2$ represents $C_1$–$C_4$ alkyl, $C_1$–$C_4$ alkenyl and $C_1$–$C_4$ alkynyl which may be substituted by halogen;
$R^3$ and $R^4$ represent independently H, $C_1$–$C_4$ alkyl or form together with the nitrogen atom a 5- or 6-membered ring;
n has the value 0 or 1;
ALK is an aliphatic hydrocarbon with 1–8 carbon atoms and their pharmaceutically acceptable salts.

These new compounds are typical monoamine reuptake blockers with additional $\alpha_2$ antagonist activity and show strong anti-depressant activity without being sedative. Compounds according to this invention are also suitable for treating patients with anxiety disorders, e.g. panic disorder.

7 Claims, No Drawings

TETRAHYDRONAPHTHALENE AND INDANE DERIVATIVES

The invention relates to tetrahydronaphthalene and indane derivatives with the general formula I:

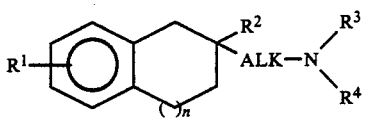

wherein
$R^1$ represents zero to four substituents, which may be the same or different and are selected from OH, halogen, $NO_2$, CN, $CF_3$, $C_1$-$C_4$ alkyl, $C_1$-$C_4$ alkoxy and unsubstituted or $C_1$-$C_4$ alkyl substituted amino;
$R^2$ represents $C_1$-$C_4$ alkyl, $C_1$-$C_4$ alkenyl and $C_1$-$C_4$ alkynyl which may be substituted by halogen;
$R^3$ and $R^4$ represent independently H, $C_1$-$C_4$ alkyl or form together with the nitrogen atom a 5- or 6-membered ring;
n has the value 0 or 1;
ALK is an aliphatic hydrocarbon with 1-8 carbon atoms; and their pharmaceutically acceptable salts.

These new compounds are typical monoamine reuptake blockers with additional $\alpha_2$ antagonist activity and show strong anti-depressant activity without being sedative. Compounds according to this invention are also suitable for treating patients with anxiety disorders, e.g. panic disorder.

Preferred compounds of formula I have an unsubstituted mono- or disubstituted aromatic nucleus and a substituent $R^2$ being $C_1$-$C_4$ alkyl, whereas $R^3$ and $R^4$ are selected from H, $C_1$-$C_4$ alkyl or together with the nitrogen atom form a piperazine or 4-methylpiperazine ring and ALK is methylene or ethylene.

Among those preferred compounds the most active compounds are tetrahydronaphthalene and especially indane derivatives, wherein the aromatic nucleus is unsubstituted and $R^2$ is $CH_3$, $R^3$ is $CH_3$ or H with a preference for H, $R^4$ is H and ALK is methylene. The term $C_1$-$C_4$ alkyl, used in the definition of general formula I, means an alkyl group with 1 to 4 carbon atoms, viz. methyl, ethyl, propyl, isopropyl, butyl, isobutyl, sec-butyl and tert-butyl.

The term $C_1$-$C_4$ alkoxy means an alkoxy group in which the term alkyl has the similar meaning as above.

The terms $C_1$-$C_4$ alkenyl and $C_1$-$C_4$ alkynyl mean unsaturated hydrocarbons of 1 to 4 carbon atoms with double or triple bonds respectively. Examples are vinyl, allyl, isopropenyl, ethynyl, 1-butynyl, and the like.

The term ALK means an aliphatic hydrocarbon with 1-8 carbon atoms, which may be branched or straight-chained. Preferably this hydrocarbon is a saturated hydrocarbon with 1-4 carbon atoms, such as the methylene, ethylene, propylene and butylene group.

The 5- and 6-membered ring, mentioned in the definition of $R^3$ and $R^4$ is a heterocyclic ring which may contain an additional hetero atom, such as pyrrolidine, piperidine, morpholine, piperazine, dihydro-imidazole, pyrazolidine, imidazolidine, this ring may be substituted with $C_1$-$C_4$ alkyl. Particularly useful are the piperazine and 4-methylpiperazine rings.

Pharmaceutical acceptable salts are acid addition salts derived from acids, such as hydrochloric acid, sulphuric acid, phosphoric acid, acetic acid, propionic acid, glycolic acid, maleic acid, fumaric acid, malonic acid, succinic acid, tartaric acid, lactic acid, citric acid, ascorbic acid, salicylic acid, benzoic acid, methanesulphonic acid, obtained by reaction of the free base according to formula I with an appropriate acid in a suitable solvent.

The compounds of this invention may be prepared by any method known for the preparation of analogous compounds.

A suitable method for the preparation of compounds I is reduction of an amide of general formula II:

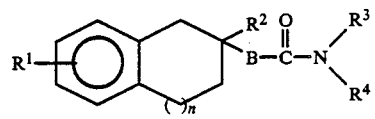

wherein $R^1$, $R^2$, $R^3$, $R^4$, and n have the aforesaid meanings, and B is a bond between the ring and the carbonyl group or is an aliphatic hydrocarbon with 1 to 7 carbon atoms.

Suitable reduction means are those commonly use in the reduction of amides, e.g. metalhydrides, and preferably $LiAlH_4$, borane or a mixture of $LiAlH_4$ and $AlCl_3$ in a suitable solvent, like, tetrahydrofuran, diethylether, benzene and the like.

Compounds of general formula I, wherein $R^3$ and $R^4$ are H, can also be obtained by reduction of a carbonitrile with general formula III:

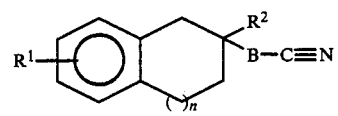

wherein $R^1$, $R^2$ and n have the aforesaid meanings.

Reduction means and solvents commonly used in the reduction of nitriles may be employed.

Compounds of general formula I, wherein $R^4$ is H may be obtained by reduction of a Schiff base of general formula IV:

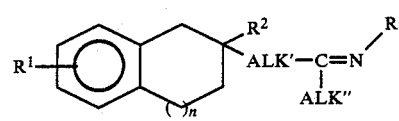

wherein $R^1$, $R^2$ and n have the aforesaid meanings, $R^3$ is hydrogen or $C_1$-$C_4$ alkyl and ALK'—C—ALK" has the same carbon atom skeleton as ALK, with a suitable reducing agent, e.g. sodium borohydride in methanol or ethanol.

Compounds according to formula I, in so far as $R^3$ and/or $R^4$ are H, may be converted into other compounds according to the invention. For example, reaction with formaldehyde and formic acid leads to compounds where $R^3$ and/or $R^4$ are $CH_3$. Reaction with alkylhalogenide leads to alkyl substitution at nitrogen, which can be performed advantageously through its trifluoroacetamide.

When compounds of the general formula I contain chiral atoms, the pure enantiomers as well as the mixtures thereof including the racemic mixture, belong to the invention.

The pure enantiomers can be obtained by stereoselective synethesis or by resolution of the racemic end product or precursors thereof.

Compounds according to this invention can be mixed with a suitable pharmaceutical carrier in order to obtain a pharmaceutical preparation for either oral, local or parenteral administration.

Preferred daily dose is between 0.01 and 50 and more preferably between 0.1 and 10 mg/kg body weight and for human use a daily dose between 5 and 500 mg is common. For the purpose of administration the compound of the invention is processed in the form suitable for oral, local or parenteral administration, for example as a tablet, pill capsule, solution, emulsion, paste or spray. The oral form is the most preferred form of administration.

The following examples further illustrate the preparation of the compounds used in this invention.

EXAMPLE 1

1,2,3,4-Tetrahydro-2,N-dimethylnaphthalene-2-methanamine (Z)-2-butenedioate (1:1)

A solution of 1,2,3,4-tetrahydro-2,N-dimethylnaphthalene-2-carboxamide (10 g) in tetrahydrofuran (90 ml) was added dropwise to a stirred suspension of lithium aluminium hydride (2.5 g) in tetrahydrofuran (10 ml) at such a rate that a gentle reflux was maintained. After the addition had been completed, the reaction mixture was refluxed for a further half hour then it was cooled and excess reagent was destroyed by careful addition of water.

The resulting mixture was filtered, and evaporation of the filtrate gave the amine as an oil. This was converted to the maleate salt in the usual manner and recrystallised from methanol/ether to give pure 1,2,3,4-tetrahydro-2,N-dimethylnaphthalene-2-methanamine (Z)-2butenedioate (1:1), mp 132°–135° C.

EXAMPLE 2

In an analogous manner as described in example 1 was prepared:

1,2,3,4-Tetrahydro-2-methylnaphthalene-2-methanamine hydrochloride, mp 211°–212° C.;

1,2,3,4-Tetrahydro-2,N,N-trimethylnaphthalene-2methanamine hydrochloride, mp 184°–195° C.;

2-Ethyl-1,2,3,4-tetrahydronaphthalene-2-methanamine hydrochloride, mp 151° C.;

2-Ethyl-1,2,3,4-tetrahydro-N-methylnaphthalene-2-methanamine hydrochloride, mp 203° C.;

1,2,3,4-Tetrahydro-2,N-dimethylnaphthalene-2-ethanamine hydrochloride, mp 201° C.;

1,2,3,4-Tetrahydro-2-(3-propenyl)-naphthalene-2methanamine hydrochloride, mp 159° C.;

1,2,3,4-Tetrahydro-N-methyl-2-(3-propenyl)-naphthalene-2methanamine hydrochloride, mp 197° C.;

6-Chloro-1,2,3,4-tetrahydro-2,N-dimethylnaphthalene-2-methanamine hydrochloride, mp 255° C.;

6-Chloro-1,2,3,4-tetrahydro-2-methylnaphthalene-2-methanamine hydrochloride, mp 193° C.;

7-Chloro-1,2,3,4-tetrahydro-2-methylnaphthalene-2-methanamine hydrochloride, mp 210° C.;

7-Chloro-1,2,3,4-tetrahydro-2,N-dimethylnaphthalene-2-methanamine hydrochloride, mp 213° C.;

1,2,3,4-Tetrahydro-6-methoxy-2,N-dimethylnaphthalene-2-methanamine hydrochloride, mp 215° C.;

1,2,3,4-Tetrahydro-7-methoxy-2,N-dimethylnaphthalene-2-methanamine hydrochloride, mp 193° C.;

2-Ethynyl-1,2,3,4-tetrahydro-N-methylnaphthalene-2-methanamine (Z)-2-butenedioate (1:1), mp 142° C. dec.;

2-Fluoromethyl-1,2,3,4-tetrahydro-N-methylnaphthalene-2-methanamine hydrochloride, mp 169° C.;

2,3-Dihydro-2,N-dimethyl-1H-indene-2-methanamine hydrochloride, mp 218° C.;

5-Chloro-2,3-dihydro-2,N-dimethyl-1H-indene-2-methanamine hydrochloride, mp 206° C.;

5,6-Dichloro-2,3-dihydro-2,N-dimethyl-1H-indene-2-methanamine hydrochloride, mp 244° C.;

2,3-Dihydro-2,N-dimethyl-1H-indene-2-ethanamine hydrochloride, mp 178° C.;

5,6-Dichloro-2,3-dihydro-2,N-dimethyl-1H-indene-2-ethanamine hydrochloride, mp 229° C.;

1-(2,3-Dihydro-2-methyl-1H-2-indenylmethyl)piperazine dihydrochloride, mp 267° C. (dec).

1-(5,6-Dichloro-2,3-dihydro-2-methyl-1H-2-indenylmethyl)piperazine dihydrochloride, mp 275° C. (dec);

1-Methyl-4-(1,2,3,4-tetrahydro-2-methyl-2-naphthalenyl methyl)piperazine dihydrochloride, mp 253° C.;

1-(1,2,3,4-Tetrahydro-2-methyl-2-naphthalenylmethyl) piperazine dihydrochloride, mp 251° C.;

EXAMPLE 3

1,2,3,4-Tetrahydro-N-methyl-2-(1-methylethyl)-naphthalene-2-methanamine hydrochloride.

A solution of borane-tetrahydrofuran complex in tetrahydrofuran (14 ml of 1M - 1 5 mole equiv.) was added to a solution of 1,2,3,4-tetrahydro-N-methyl-2-(1-methylethyl)-naphthalene-2-carboxamide (2.1 g) in tetrahydrofuran (5 ml). The resulting solution was left standing at room temperature for eleven days, then it was acidified with hydrochloride acid and refluxed for eight hours.

The reaction mixture was diluted with water and extracted with ether. The aqueous phase was then made strongly alkaline with ammonium hydroxide, and the product was extracted into ether.

Passage of gaseous hydrogen chloride gave a precipitate of the salt which was isolated by filtration and recrystallized from methanol/ether to give 1,2,3,4-tetrahydro-N-methyl-2-(1-methylethyl)-naphthalene-2-methanamine hydrochloride (1.2 g), mp 261° C.

EXAMPLE 4

1,2,3,4-Tetrahydro-2-(1-methvlethvl)-naphthalene-2-methanamine (Z)-2-butenedioate (1:1)

A solution of 1,2,3,4-tetrahydro-2-(I-methylethyl)-naphthalene-2-carbonitrile (3.5 g) in dry ether (35 ml) was added dropwise to a stirred suspension of lithium aluminium hydride (1.5 g) in dry ether (1.5 ml). The reaction mixture was then refluxed for thirty minutes.

After excess reagent had been destroyed by careful addition of water, the mixture was filtered and the filtrate was evaporated to an oil (3.4 g). The crude amine was converted to the maleate salt and crystallized from methanol/ether to give: 1,2,3,4-tetrahydro-2-(1-methylethyl)-naphthalene-2-methanamine (Z)-2-butenedioate (1:1) (4 g), mp 109° C.

EXAMPLE 5

In an analogous manner as described in Example 4 was prepared:

2,3-Dihydro-2-methyl-1H-indene-2-methanamine hydrochloride, mp 228° C.;

5-Chloro-2,3-dihydro-2-methyl-1H-indene-2-methanamine hydrochloride, mp 217° C.;
1,2,3,4-Tetrahydro-2-methylnaphthalene-2-ethanamine hydrochloride, mp 216° C.;
1,2,3,4-Tetrahydro-2-methylnaphthalene-2-propanamine hydrochloride, mp 129° C.;

EXAMPLE 6

N-Ethyl-1,2,3,4-tetrahydro-2-methylnaphthalene-2-methanamine hydrochloride.

Trifluoroacetic anhydride (14.2 ml) was added dropwise to a solution of 1,2,3,4-tetrahydro-2-methylnaphthalene-2-methanamine (117 g) and triethylamine (10 ml) in dichloromethane (100 ml) at 10°–15° C. When the addition had been completed, water was added and the layers were separated. The organic layer was washed three times with water, then dried over sodium sulphate and evaporated to give the trifluoroacetamide (18 g), mp 73° C.

Finally powdered potassium hydroxide (3.3 g) was added all at once to a solution of the trifluoroacetamide (4 g) in dry acetone (100 ml) and iodoethane (4.7 ml) just as it reached boiling point. The mixture was refluxed for half an hour, then the solvent and excess iodoethane were distilled off under reduced pressure. The residue was refluxed with 50% aqueous acetone (100 ml) for half an hour, then the mixture was extracted with ether and evaporated to give crude N-ethyl-1,2,3,4-tetrahydro-2-methylnaphthalene-2-methanamine (3 g). This material was purified by chromatography on silica gel eluted with dichloromethane containing an increasing proportion of methanol and ammonium hydroxide, and the purified amine was converted to the hydrochloride salt. Recrystallization from methanol/ether gave N-ethyl-1,2,3,4-tetrahydro-2-methylnaphthalene-2-methanamine hydrochloride (1.8 g), mp 180° C.

EXAMPLE 7

In an analogous manner as described in Example 6 was prepared:
1,2,3,4-tetrahydro-N-methyl-2-(3-propenyl)-naphthalene-2-methanamine hydrochloride, mp 197° C.;

EXAMPLE 8

2-Ethyl-1,2,3,4-tetrahydro-N,N-dimethylnaphthalene-2-methanamine hydrochloride.

A solution of 2-ethyl-1,2,3,4-tetrahydro-N-methylnaphthalene-2-methanamine (3g) in formic acid (4.5 ml) and 40% aqueous formaldehyde (4.5 ml) was heated at 90° C. for six hours. The resulting solution was cooled, diluted with water, and basified with sodium hydroxide solution. The product was extracted with ether and the extract was dried over sodium sulphate. Passage of gaseous hydrogen chloride gave a precipitate of the salt which was collected and recrystallized from dichloromethane/ether to give 2-ethyl-1,2,3,4-tetrahydro-N,N-dimethylnaphthalene-2-methanamine hydrochloride (1.2 g), mp 157° C.

EXAMPLE 9

In an analogous manner as described in Example 8 was prepared:
1,2,3,4-Tetrahydro-N,N-dimethyl-2-(3-propenyl)-naphthalene-2-methanamine hydrochloride;
1,2,3,4-Tetrahydro-N,N-dimethyl-2-(1-methylethyl)-naphthalene-2-methanamine hydrochloride, mp 195° C.

EXAMPLE 10

2,3-Dihydro-2N,α-trimethyl-1H-indene-2-methanamine hydrochloride

2-Acetyl-2,3-dihydro-2-methyl-1H-indene (3 g) was dissolved in a solution of methylamine in ethanol (15 ml; 33% w/w) and the solution was allowed to stand at room temperature for 16 h. Sodium borohydride (750 mg) was added to the solution and after 1 h the solution was evaporated to a small volume and water was added. The amine was isolated by extraction into ether and converted in the usual manner to the hydrochloride salt which was crystallized from methanol to give the titled compound (2 g), m.p. 254° C.

We claim:
1. A tetrahydronaphthalene or indane compound of the

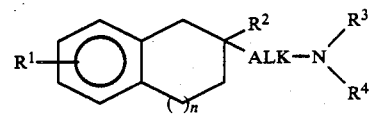

wherein
R$^1$ represents a zero to four substituents, which may be the same or different and are selected from OH, halogen, NO$_2$, CN, CF$_3$, C$_1$–C$_4$ alkyl, C$_1$–C$_4$ alkoxy and unsubstituted or C$_1$–C$_4$ alkyl substituted amino;
R$^2$ represents C$_1$–C$_4$ alkyl, C$_1$–C$_4$ alkenyl an C$_1$–C$_4$ alkynyl which may be substituted by halogen;
R$^3$ and R$^4$ represent independently H, C$_1$–C$_4$ alkyl or form together with the nitrogen a 5- or 6-membered ring which may contain an additional nitrogen or oxygen;
n has the value 0 or 1; and
ALK is an aliphatic hydrocarbon with 1–8 carbon atoms selected from the group consisting of saturated hydrocarbons, hydrocarbons with double bonds and hydrocarbons with triple bonds, or its pharmaceutically acceptable salt.

2. Compound according to claim 1, having an unsubstituted, mono- or disubstituted aromatic nucleus, wherein R$^2$ is C$_1$–C$_4$ alkyl, R$^3$ and R$^4$ are H, C$_1$–C$_4$ alkyl or together with the nitrogen form a piperazine or 4-methylpiperazine ring, ALK is methylene or ethylene, or its pharmaceutically acceptable salt.

3. Compound according to claim 1, wherein the aromatic nucleus is unsubstituted, R$^2$ is CH$_3$, R$^3$ is CH$_3$ or H, R$^4$ is H, ALK is methylene, and n is 0 or 1, or its pharmaceutically acceptable salt.

4. Compound according to claim 1, wherein the aromatic nucleus is unsubstituted, R$^2$ and R$^3$ are CH$_3$, R$^4$ is H, ALK is methylene, and n is 0 or 1, or its pharmaceutically acceptable salt.

5. Compound according to claim 1, wherein the aromatic nucleus is unsubstituted, R$^2$ is CH$_3$, R$^3$ and R$^4$ are H, ALK is methylene, and n is 0, or its pharmaceutically acceptable salt.

6. Pharmaceutical preparation comprising a compound according to claim 1 in an effective amount for monoamine reuptake blocking activity in admixture with a pharmaceutically acceptable carrier.

7. Method for treating depression in a human patient comprising administering an effective amount of at least one compound according to claim 1.

* * * * *